United States Patent [19]

White et al.

[11] Patent Number: 5,176,879
[45] Date of Patent: Jan. 5, 1993

[54] ANIMAL LITTER COMPOSITION HAVING DEODORIZING PROPERTIES

[75] Inventors: Michael P. White; Anne D. Woodbury, both of Little Rock, Ark.

[73] Assignee: Rhone-Poulenc, Inc., Monmouth Junction, N.J.

[21] Appl. No.: 673,370

[22] Filed: Mar. 22, 1991

[51] Int. Cl.⁵ ............................................. A61L 11/00
[52] U.S. Cl. ........................................ 422/5; 119/171; 119/173; 424/76.5; 424/76.6
[58] Field of Search ................... 119/171, 173; 422/5; 424/76.5, 76.6

[56] References Cited

U.S. PATENT DOCUMENTS

| 2,895,873 | 7/1959 | Sawyer, Jr. et al. | 119/173 |
| 3,029,783 | 4/1962 | Sawyer, Jr. et al. | 119/173 |

FOREIGN PATENT DOCUMENTS

| 2207463 | 9/1987 | Japan | 424/76.6 |
| 2238834 | 9/1990 | Japan | 119/171 |

Primary Examiner—Robert J. Warden
Assistant Examiner—Stephanie Blythe
Attorney, Agent, or Firm—Herbert P. Price

[57] ABSTRACT

Animal litters having deodorizing properties are made from particulate moisture absorbent material and aluminum salts.

4 Claims, No Drawings

ANIMAL LITTER COMPOSITION HAVING DEODORIZING PROPERTIES

BACKGROUND OF THE INVENTION

The field of art to which this invention pertains is animal litter compositions.

In order to be useful in animal litter, materials must have good water or moisture absorbency and should have the capacity to eliminate or substantially reduce odors, particularly ammonical odors which normally result from animal waste.

Various clays, such as those based on the clay minerals kaolinite, illite, attapulgite, montmorillonite, sepiolite, diatonite, and the like, have been used extensively in animal litter compositions due to their water and moisture absorbing properties. However, such clays have very little, if any, deodorizing properties.

In U.S. Pat. No. 4,157,696, animal litter pellets which have moisture absorbency and deodorizing capability are made from flyash and cellulosic materials plus clays such as bentonite and kaolin.

U.S. Pat. No. 4,704,989 discloses pelletizing clay fines with deodorizers, bacteriocides, antioxidants and mold inhibitors to form cat box absorbents. Deodorizers, such as pine oil, wintergreen, sodium bicarbonate, chlorophyll, sodium dihydrogen phosphate, potassium dihydrogen phosphate, potassium acid phthalate, the water-soluble constituents of cherry pits, 2-isopropoxycamphane and 2(beta-hydroxy-ethoxy) camphane, are listed.

Animal litter compositions having deodorizing capability are described in U.S. Pat. No. 4,258,660. Such compositions are pellets of straw, sunflower hulls and dried alfalfa bound together with a bentonite clay.

In U.S. Pat. No. 4,914,066, moisture absorbent pellets useful as animal litter are made from a blend of bentonite clay and solid water-swellable but water-insoluble polymeric hydrocolloids.

Various processes for making water absorbent clay products are described in U.S. Pat. Nos. 4,591,581; 4,343,751; and 3,935,363.

SUMMARY OF THE INVENTION

This invention is directed to animal litter compositions having both moisture absorbency and deodorizing capability.

The animal litter compositions used in this invention are made from blends of moisture absorbent particulate materials and aluminum salts wherein the aluminum salt is present in the blends in the amount of about 5 to about 20 weight percent based on the weight of moisture absorbent particulate materials. Such blends can be made by adding an aqueous solution of the aluminum salt to the particulate material, intimately mixing the components, and drying the mixture to a moisture content below about 10 weight percent.

Animal litter compositions can also be made from the residue obtained from the process of making aluminum salts by the reaction of inorganic acids on aluminum containing clay minerals.

DETAILED DESCRIPTION OF THE INVENTION

The moisture absorbent particulate material used in this invention is organic or inorganic particulate material which is insoluble in water but which is capable of absorbing water.

Examples of organic moisture absorbent particulate material useful in this invention are naturally occurring cellulose materials, such as wood saw dust, crushed corncobs, cotton linters, wood pulp, straw, sunflower hulls, dried alfalfa and the like. Preferably when using such cellulosic materials, they are bound together and pelletized with a clay, e.g., bentonite clay, using the procedure described in U.S. Pat. No. 4,258,660 which is hereby incorporated by reference.

Other useful moisture absorbent materials are the so-called super-absorbent polymers which are water swellable organic polymeric hydrocolloids insoluble in water but capable of absorbing water. These hydrocolloids are polymers of water soluble acrylic or vinyl monomers which are slightly crosslinked with a polyfunctional reactant. Such polymeric hydrocolloids and pellets made from the hydrocolloids and bentonite clays are described in detail in U.S. Pat. No. 4,914,066 which is hereby incorporated by reference.

Preferred moisture absorbent materials for use in this invention are water absorbent clays. Such clays generally fall into such groups as the kaolin group, montmorillonite group, the illite or mica clay mineral group, the chlorite group, the vermiculite group, the polygorskite group which includes attapulgite, the sepiolite group as well as allophane and bauxitic clays. Moisture absorbing clays are well known and are described in detail in "Encyclopedia of Chemical Technology" 2nd Edition, by Kirk-Othmer, Vol 5, pp 541–557, which is hereby incorporated by reference. Useful clays are those which are capable of absorbing at least 25 percent of their weight in water, and preferably at least 50 percent.

The aluminum salts useful in this invention are the water soluble salts of aluminum and the anions of inorganic acids, examples of which are aluminum chloride, aluminum nitrate, aluminum phosphate and aluminum sulfate. Additional aluminum salts useful in this invention are the "alums," i.e., hydrated double sulfates of aluminum and univalent cations such as potassium, sodium, and ammonium. The preferred aluminum salt is aluminum sulfate.

In preparing the animal litter compositions of this invention, the aluminum salt is added to the particulate moisture absorbent material, generally as a spray, and is mixed until a uniform blend is obtained. The blend is then dried, if necessary, to a moisture content below about 10 weight percent, and, preferably, to about 5 to about 8 weight percent wherein said weight percent is based on the total weight of the blend.

The blends of aluminum salt and particulate moisture absorbent material useful as animal litter can also be made from the residue, or by-product, obtained from the process of making aluminum salts by the reaction of inorganic acids on aluminum containing clay minerals. When acids, e.g., hydrochloric or sulfuric acid, are reacted with aluminum containing clay minerals, e.g., bauxitic clays, or kaolin, to form aluminum salts, the residue, after the salts are removed, is comprised of moisture absorbent clay, which is referred to as mud in the trade, and a small amount of aluminum salt. When dried to a moisture content below about 10 weight percent, such by-products can be used as animal litters which have deodorizing properties.

A particularly preferred composition for use as an animal litter is the residue or by-product, obtained in the manufacture of aluminum sulfate from kaolin. In the aluminum sulfate process, kaolin is heated, for example, to about 750° C., to drive out water of crystallization and to convert the kaolin to a crystal structure known as meta kaolin. The meta kaolin is then digested in sulfuric acid at temperatures of about 90° C. to about 110° C. to convert the alumina in the kaolin to aluminum sulfate. The aluminum sulfate is recovered as an aqueous solution, leaving mineral residue which is predominantly silica with a small amount of alumina plus aluminum sulfate which is not removed in the extracting and washing steps of the process. The residue is dried to a moisture content below about 10 weight percent, preferably about 5 to about 8 weight percent. The resulting composition contains about 2 to about 10 weight percent aluminum sulfate. The weight percents are based on the weight of the dried composition.

This composition can be used as an animal litter without further treatment. However, in order to obtain an animal litter which has deodorizing capability as well as water absorbent properties, the aluminum sulfate content of the residue is adjusted, if necessary, with additional aluminum sulfate to obtain a composition having about 5 to about 20 weight percent aluminum sulfate, preferably about 6.7 to about 10 weight percent.

Meta kaolin, which is obtained when kaolin is heated to drive off chemically bound water, has a collapsed crystal structure. After treatment with sulfuric acid and the removal of alumina as aluminum sulfate, the residual mineral has open spaces in its structure in which water can be absorbed. This residue can absorb up to about 125 weight percent water based on its weight, generally about 75 to about 100 percent.

The particulate moisture absorbent material-aluminum salt compositions can be used for animal litter preferably in small particle form or as pellets. When used in particulate form, the size will vary from about -16 to about +60 mesh, U.S. Standard Sieve, i.e., about 0.25 mm to about 1.2 mm. The compositions can also be pelleted using procedures such as those described in U.S. Pat. Nos. 4,914,066, 4,591,581, and 4,704,989 which are hereby incorporated.

Moisture absorbing materials which contain in admixture therewith aluminum salts have the capacity not only to absorb moisture but to reduce and to eliminate odors, particularly ammonia. Such compositions are particularly useful as animal litter to absorb and to deodorize liquid waste of animals, such as cats.

When used as kitty litter, particulate moisture absorbent materials which contain aluminum salts in the amount of about 5 weight percent up to about 20 weight percent rapidly absorb and deodorize liquid animal waste. Particularly useful compositions are those based on moisture absorbing clay minerals and aluminum sulfate.

The following examples describe the invention in more detail. Parts and percentages unless otherwise designated are parts and percentages by weight.

EXAMPLE

The residue from a kaolin—aluminum sulfate process had a residual aluminum sulfate content of 2.2 percent based on the weight of the residue. This composition is designated as Composition 1.

The residue from another kaolin-aluminum sulfate process had a residual aluminum sulfate content of 7.4 weight percent. This composition is designated as Composition 2.

To Composition 1 was added a solution of aluminum sulfate in water in the amount of 16.75 percent aluminum sulfate based on the weight of the residue, i.e., to 100 parts of the residue were added 16.75 parts of aluminum sulfate. This composition is designated as Composition 3.

To Composition 1 was added a solution of aluminum sulfate in water in the amount of 10 percent. This composition is designated as Composition 4.

To Composition 1 was added a solution of aluminum sulfate in the amount of 3.35 percent. This composition is designated as Composition 5.

All of these compositions were dried to approximately the same moisture content below 10 percent.

Composition 6 and Composition 7 were commercial kitty litters.

These compositions were tested for water absorbency and odor absorbency by adding to each composition an equal amount of a 3 percent ammonium hydroxide solution by volume observing the absorbence and then smell testing by 7 people. Initially all of the products controlled odor. More and more ammonium hydroxide was added until the ammonia odor could be detected in each product. The products were rated with the lowest number being the litter which performed best.

| Composition | % $Al_2(SO_4)_3$ | Deodorizing Ability |
|---|---|---|
| 1 | 2.2 | 5 |
| 2 | 7.4 | 3 |
| 3 | 19 | 1 |
| 4 | 12.2 | 2 |
| 5 | 5.5 | 4 |
| 6 | 0 | 6 |
| 7 | 0 | 6 |

The deodorizing property is directly proportional to the amount of aluminum sulfate in the composition. All of the compositions had good moisture absorbent properties.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. In a method of deodorizing and absorbing animal waste liquid by contacting the animal waste liquid with an absorbent, the improvement which comprises using as the absorbent residue obtained in the manufacture of aluminum sulfate from kaolin, wherein said residue includes silica, alumina and about 2 to about 10 weight percent aluminum sulfate, wherein said weight percent is based on the weight of the residue.

2. The method of claim 1 wherein the aluminum sulfate is present in the amount of about 6.7 to about 10 weight percent.

3. The method of claim 1 wherein the residue is obtained by (a) heating kaolin to about 750° C. to convert the kaolin to meta kaolin, (b) digesting the meta kaolin in sulfuric acid at a temperature of about 90°-110° C. to convert alumina in the meta kaolin to aluminum sulfate, (c) removing aluminum sulfate as an aqueous solution from the residue, (d) washing the residue and (e) drying the residue to a moisture content below 10 weight percent.

4. The method of claim 3 wherein the residue is dried to a moisture content of about 5 to about 8 weight percent.

* * * * *